(12) United States Patent
Norris

(10) Patent No.: US 11,583,429 B2
(45) Date of Patent: Feb. 21, 2023

(54) LEG STRAP ASSEMBLY FOR A URINE BAG

(71) Applicant: Temeka Norris, Bolingbrook, IL (US)

(72) Inventor: Temeka Norris, Bolingbrook, IL (US)

(*) Notice: Subject to any disclaimer, the term of this patent is extended or adjusted under 35 U.S.C. 154(b) by 0 days.

(21) Appl. No.: 16/916,327

(22) Filed: Jun. 30, 2020

(65) Prior Publication Data

US 2021/0401612 A1    Dec. 30, 2021

(51) Int. Cl.
*A61F 5/44*    (2006.01)

(52) U.S. Cl.
CPC ................... *A61F 5/4408* (2013.01)

(58) Field of Classification Search
CPC .......... A61F 5/4408; A61F 5/44; A61F 5/449; A61M 2025/0206; A61M 25/02; A61M 2209/088; A61M 2025/0213; A61M 2025/026; A41D 1/00; Y10S 128/26; A41F 9/002; A45C 13/30; A45F 2005/008
See application file for complete search history.

(56) References Cited

U.S. PATENT DOCUMENTS

| | | | |
|---|---|---|---|
| 722,474 A | 3/1903 | Bauer | |
| 1,377,903 A | 5/1921 | Manny et al. | |
| 1,647,299 A | 11/1927 | Otto | |
| 2,437,585 A * | 3/1948 | Zimmern | A47D 15/006 |
| | | | D29/101.1 |
| D267,434 S | 12/1982 | Hubbard et al. | |
| 5,375,265 A * | 12/1994 | Selzer | A61F 5/4408 |
| | | | 2/243.1 |
| D359,809 S | 6/1995 | Vann et al. | |
| D364,798 S | 12/1995 | Bright et al. | |
| D382,055 S | 8/1997 | Cassidy et al. | |
| D397,549 S | 9/1998 | Edwards | |
| D399,054 S | 10/1998 | Garrison | |
| 6,129,709 A * | 10/2000 | Millen | A61F 5/449 |
| | | | 604/179 |
| 6,152,915 A * | 11/2000 | Watson | A61M 25/02 |
| | | | 604/353 |
| D477,873 S | 7/2003 | Borash et al. | |
| D481,534 S | 11/2003 | Andrew | |
| D563,666 S | 3/2008 | Davis | |
| D676,425 S | 2/2013 | Nishimura et al. | |
| 8,505,683 B1 * | 8/2013 | Dirrig | A63B 27/00 |
| | | | 182/9 |

(Continued)

FOREIGN PATENT DOCUMENTS

GB    2215211 A  *  9/1989  ............... A61F 5/44

OTHER PUBLICATIONS

Design U.S. Appl. No. 29/739,894, entitled "Leg Straps," filed Jun. 30, 2020.

(Continued)

*Primary Examiner* — Benjamin J Klein
*Assistant Examiner* — Alessandro R Del Priore
(74) *Attorney, Agent, or Firm* — Frost Brown Todd LLP

(57) ABSTRACT

A leg strap assembly is provided for supporting a urine bag on a user's leg. The leg strap assembly includes a pair of straps selectively couplable with the urine bag, wherein each strap of the leg strap assembly includes a central band and a pair of outer bands extending outward from each end portion of the central band. The central band has a larger width than the each of the outer bands to provide comfort to the user.

18 Claims, 9 Drawing Sheets

(56) References Cited

U.S. PATENT DOCUMENTS

| | | | |
|---|---|---|---|
| 8,618,393 B1* | 12/2013 | Peters | G10D 1/08 |
| | | | 84/327 |
| D700,707 S | 3/2014 | Baumgarten | |
| D749,743 S | 2/2016 | O'Connor | |
| D809,149 S | 1/2018 | Tsuzuranuki et al. | |
| D813,402 S | 3/2018 | Irwin-Lincoln | |
| D836,744 S | 12/2018 | Hubbard | |
| D863,564 S | 10/2019 | Herder et al. | |
| D879,101 S | 3/2020 | Li | |
| D885,592 S | 5/2020 | Dunmore | |
| D891,626 S | 7/2020 | Xu | |
| D931,442 S | 9/2021 | Gajadhar | |
| D936,232 S | 11/2021 | Jacobson | |
| 2009/0014010 A1* | 1/2009 | Leckie | A61M 25/02 |
| | | | 128/207.17 |
| 2014/0107601 A1* | 4/2014 | Branch | A61F 5/4408 |
| | | | 604/327 |
| 2015/0088081 A1 | 3/2015 | Hakel | |
| 2017/0079571 A1 | 3/2017 | Washington | |
| 2018/0289085 A1 | 10/2018 | Strange | |
| 2019/0134362 A1* | 5/2019 | Fee | A61M 25/02 |
| 2019/0247221 A1* | 8/2019 | Doherty | A61M 27/00 |
| 2019/0314188 A1* | 10/2019 | Barrientos | A61F 5/4408 |
| 2020/0368473 A1* | 11/2020 | Reyes | A61M 16/0465 |

OTHER PUBLICATIONS

Artibetter 4pacs Catheter Holder Leg Holder Adjustable Catheter Fixation Tape Urinary Leg Band Strap Wrap Holder (White); Artibetter; Post Date Sep. 15, 2020; Seen at URL: https://www.amazon.com/ARTIBETTER-Catheter-Adjustable-Fixation-Urinary/dp/B08J3V3KC5/ref=sr_1_83?; 2020.

Catheter Leg Bag Support/Strap; Capable Clothing; Post Date Unknown; Website captured on Dec. 13, 2021, Seen at URL: https://www.capableclothing.com/products/catheter-leg-bag-support-strap; 2021.

Drain Bags: Leg Drain Bags with Elastic Straps, Twist Valve, Medium, 20-oz.; Medline Industries; Post Date Unknown; Website captured on Dec. 13, 2021, Seen at URL: https://www.byramhealthcare.com/product-and-services/catalog/urology/product/13404-drain-bags-leg-drain-bags-with-elastic-straps-twist-valve-medium-20-oz; 2021.

* cited by examiner

US 11,583,429 B2

LEG STRAP ASSEMBLY FOR A URINE BAG

BACKGROUND

A catheter is typically used to drain urine from a bladder into a urine bag for users that need help emptying their bladders. As shown in FIG. 1, a typical urine bag (10) is attached to a lower leg portion (2) (e.g., calf, shin, ankle, etc.) of the user with straps (14, 16). The urine bag (10) is then attached to a bottom end of the catheter or tubing (12) that extends along an upper leg portion (4) (e.g., thigh, knee, hip, etc.) to the bladder. Accordingly, the catheter (12) can be used to empty urine from the bladder to the urine bag (10) attached to the lower leg portion (2). Because the urine bag is typically attached to the lower leg portion of the user, it can be uncomfortable to repeatedly bend over to empty and/or change the urine bag. Moreover, the thin straps used to attach the urine bag to the lower leg portion can dig into the user's skin, causing sores, during use of the urine bag, especially as the urine bag fills.

Accordingly, it may be desirable to provide a leg strap assembly for use with a urine bag having wider straps that are sufficiently sized to support the urine bag on an upper leg portion of a user. This may provide more comfort during emptying and/or changing of the urine bag by decreasing the distance needed to reach the urine bag. This may also provide more comfort during use of the urine bag by inhibiting the straps from injuring a user's leg.

While a variety of leg straps for a urine bag have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements.

Figure 1:
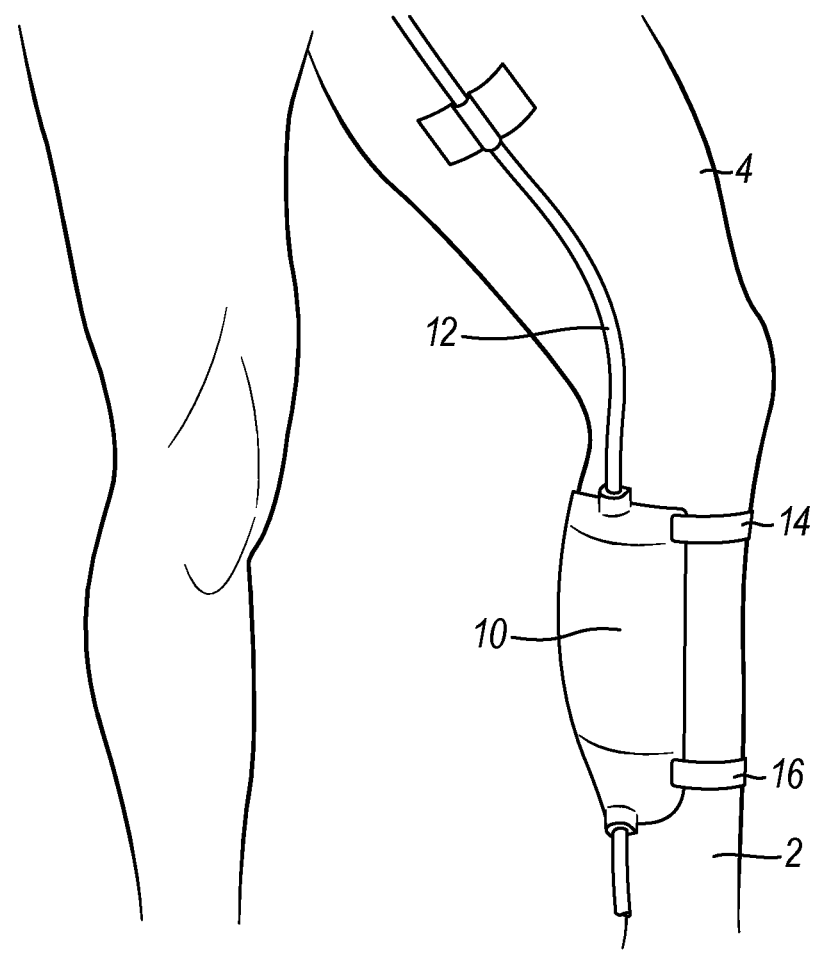
FIG. 1 depicts a schematic of a prior art urinary bag assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, spatial terms such as "under," "above," "upper," and "lower" also are used herein for reference to relative positions and directions. Such terms are used below with reference to views as illustrated for clarity and are not intended to limit the invention described herein.

In some instances, it may be desirable to provide a leg strap assembly for use with a urine bag having wider strap portion to support a urine bag on a user. This can allow the straps to be attached to an upper leg portion of the user and/or inhibit the straps from injuring the user's leg. Accordingly, such a leg strap assembly is more comfortable and can reduce injury during emptying, changing, and/or wearing a urine bag.

I. AN EXEMPLARY LEG STRAP ASSEMBLY

FIGS. 2-4B show an exemplary leg strap assembly (20) comprising a lower strap (22) and an upper strap (24). Lower and upper straps (22, 24) are sufficiently sized to wrap around an upper leg portion (4) of a user. In the illustrated embodiment, upper strap (24) is sufficiently sized to wrap around an upper portion of a user's thigh and lower strap (22) is sufficiently sized to wrap around a lower portion of a user's thigh below upper strap (24). Accordingly, lower strap (22) has a smaller length and/or width than upper strap (24). While leg strap assembly (20) is shown having two straps (22, 24), any other suitable number of straps (22, 24) can be used.

Lower strap (22) includes a central band (26) and a pair of outer bands (23) extending outwardly from each end portion of central band (26). Central band (26) has an interior surface (30) and an exterior surface (32). In the illustrated embodiment, each end portion of central band (26) is covered with a cap portion (31) that extends from the interior surface (30) around to the exterior surface (32). Caps (31) may include a sufficiently smooth material to provide a sufficiently comfortable transition at each end portion of central band (26) to inhibit central band (26) from irritating a user's leg. It should be noted that cap portions (31) are merely optional.

Figure 3A:
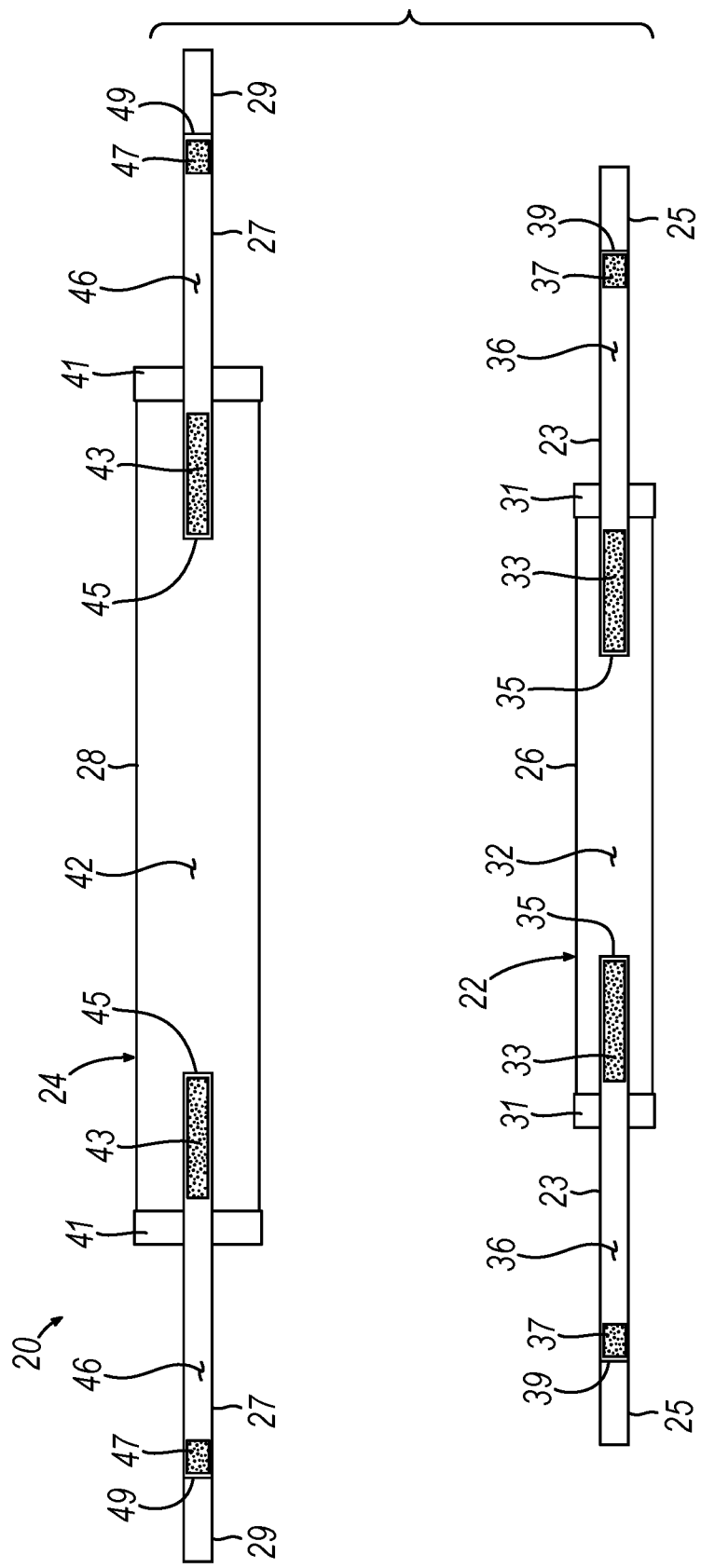
FIG. 3A depicts a rear view of the leg strap assembly of FIG. 2, shown in an unattached position.
Figure 3B:
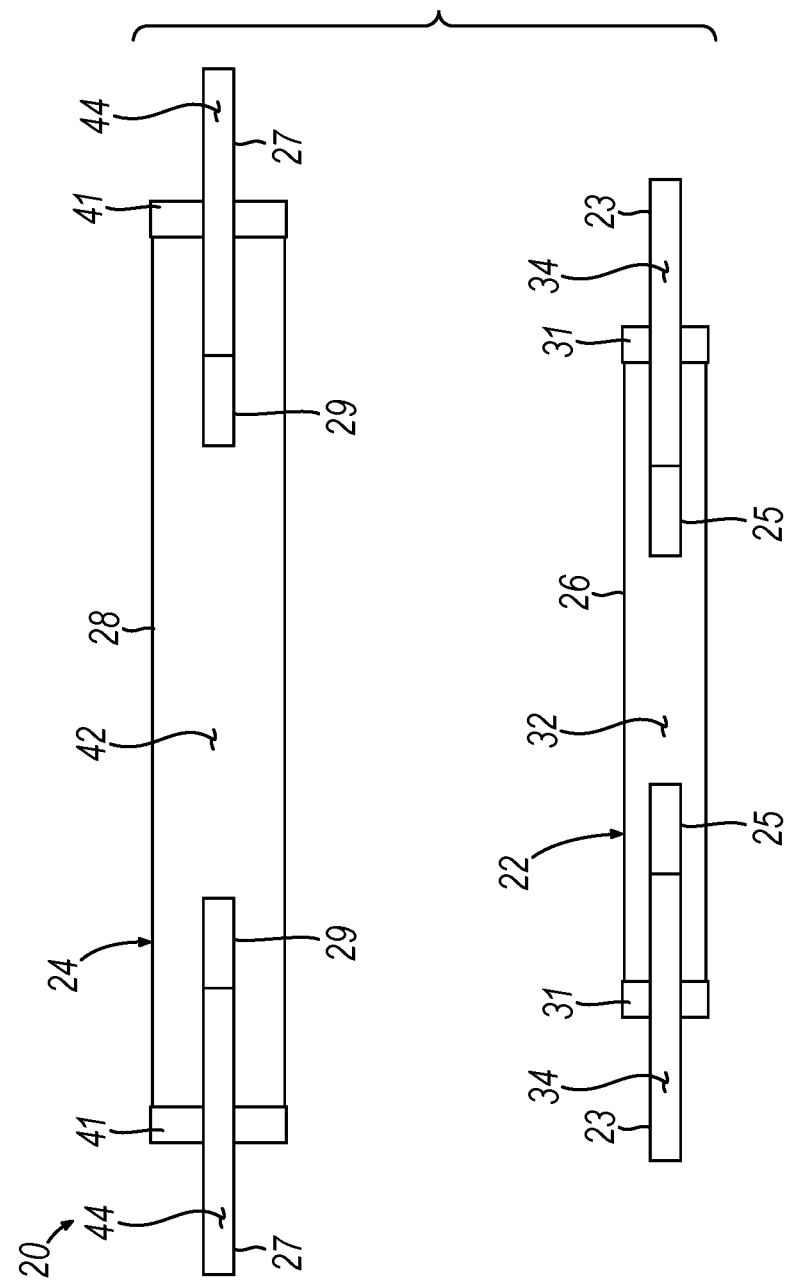
FIG. 3B depicts a rear view of the leg strap assembly of FIG. 2, shown in an attached position.
Figure 4A:
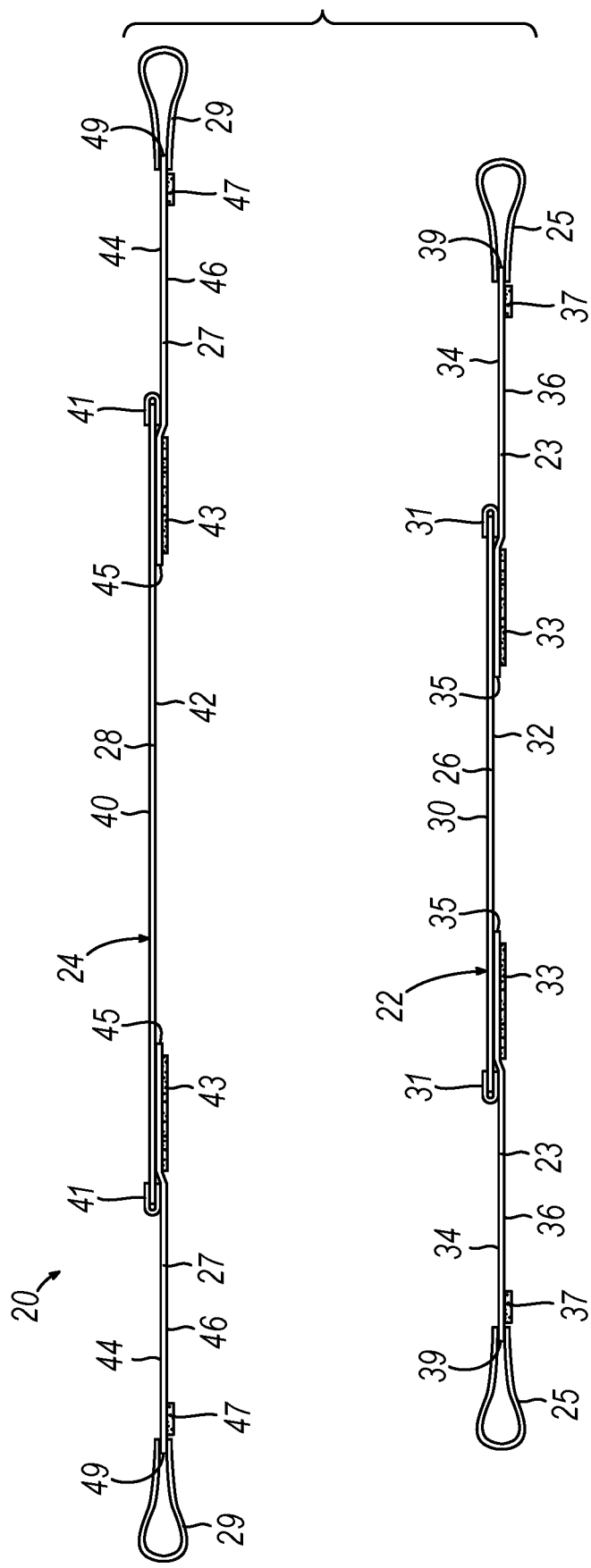
FIG. 4A depicts a top view of the leg strap assembly of FIG. 2, shown in the unattached position.
Figure 4B:
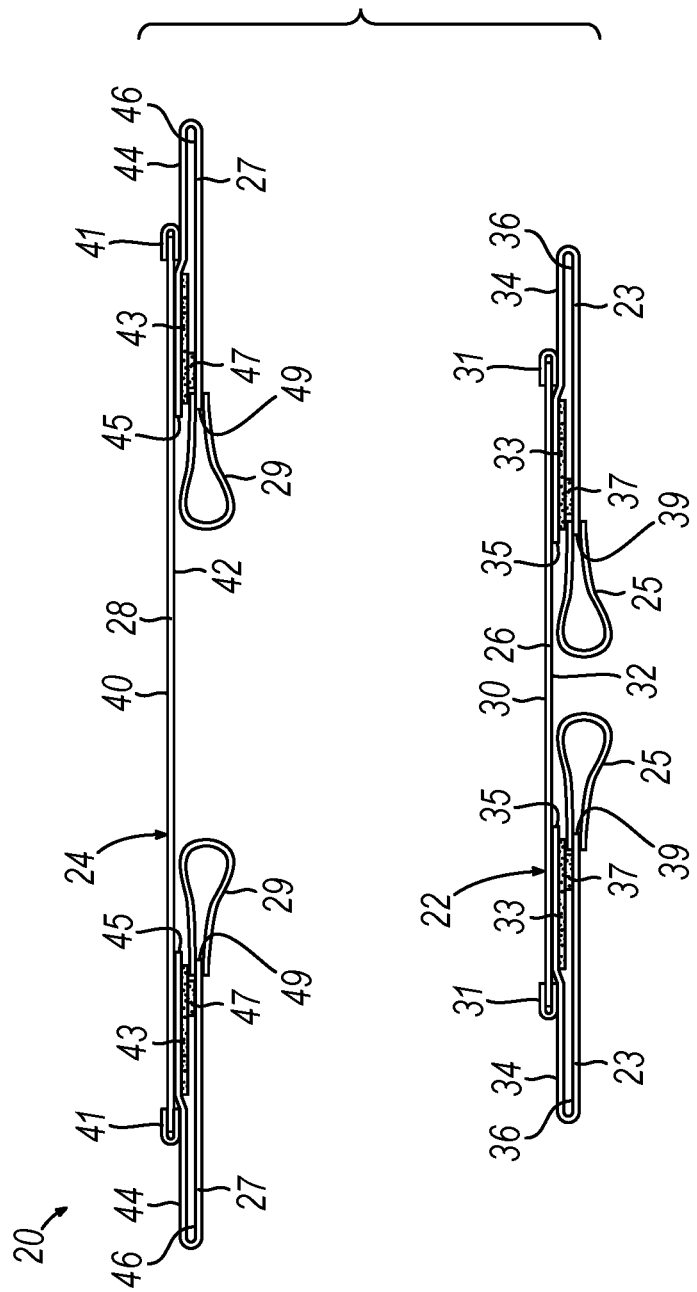
FIG. 4B depicts a top view of the leg strap assembly of FIG. 2, shown in the attached position.

Each outer band (23) of lower strap (22) has an interior surface (34) and an exterior surface (36). As best seen in FIG. 3A, interior surface (34) of each outer band (23) is secured to exterior surface (32) of central band (26). For instance, a first end (35) of each outer band (23) is secured to each end portion of central band (26) from first end (35) of outer band (23) to cap portion (31) of central band (26). Each outer band (23) may be coupled with central band (26) via sewing, adhesive, or other suitable methods. A portion of each outer band (23) secured to central band (26) includes a first coupling (33) on exterior surface (36) of outer band (23). Each outer band (23) then extends outwardly from central band (26) to a free end (39) of outer band (23). A portion of each outer band (23) at free end (39) includes a second coupling (37) on exterior surface (36) of outer band (23). A portion of second coupling (37) is configured to be selectively coupled with a portion of first coupling (33), as shown in FIGS. 3B and 4B. In the illustrated embodiment, first and second couplings (33, 37) comprise hook and loop fasteners, though other suitable couplings may be used, such as snaps, buttons, adhesives, etc. First and second couplings (33, 37) are positioned on exterior surface (36) of each outer band (23), which are coupled to exterior surface (32) of central band (26), such that interior surfaces (30, 34) of lower strap (22) are sufficiently smooth relative to exterior surfaces (32, 36). This may allow interior surfaces (30, 34) to be positioned against a user's leg to inhibit irritation and/or injuries to the user's leg.

Free end (39) of each outer band (23) of lower strap (22) further includes a handle (25) extending outwardly from free end (39) of each outer band (23). In the illustrated embodiment, each handle (25) is formed by a loop of material, though other suitable configurations for providing a suitable gripping portion may be used. Accordingly, handle (25) may be provided to allow a user to grip handle (25) to adjust the tightness of lower strap (22) about the user's leg even if the user has limited dexterity. In the illustrated embodiment, each handle (25) is sized to receive a user's thumb or finger within the loop of handle (25) for adjustment of lower strap (22). Handle (25) may be secured with each free end (39) of outer band (23) by sewing, adhesive, or other suitable method.

In the illustrated embodiment, central band (26) of lower strap (22) has a greater width than the pair of outer bands (23). For instance, central band (26) may have a width of from about ½ inch to about 2 inches, such as about 1¼ inches and each outer band (23) may have a width of from about ½ to about 1½ inches, such as about ¾ inches, though other suitable dimensions can be used. In some versions, the width of each outer band (23) is about 60% of the width of central band (26), though other suitable dimensions can be used. Central band (26) may have a length of about 10½ inches to about 12½ inches, though other suitable dimensions can be used. Each outer band (23) may have a length of from about 5 inches to about 10 inches, such as about 7 inches, though other suitable dimensions can be used. In some versions, each outer band (23) extends about 4 inches beyond central band (26), though other suitable dimensions can be used. Each handle (25) may have a length of from about 1 inch to about 2 inches and a width that is similar to the width of the corresponding outer band (23), though other suitable dimensions can be used. First coupling (33) may have a length of from about 1 inch to about 3 inches, such as about 2½ inches, and a width that is similar to the width of the corresponding outer band (23), though other suitable dimensions can be used. Second coupling (37) may have a length of from about ½ inch to about 2 inches, such as about 1 inch, and a width that is similar to the width of the corresponding outer band (23), though other suitable dimensions can be used. Accordingly, second coupling (37) has a smaller length than first coupling (33). In some versions, second coupling may have a length that is about 40% of the length of first coupling (33), though other suitable dimensions can be used.

Central band (26) of lower strap (22) is made from a first flexible material that is sufficiently elastic to adjust to each user's leg. For instance, central band (26) can be made from a sport elastic, which may comprise about 70% polyester and about 30% rubber. This may provide a softer elastic to provide more comfort in a knee area of a patient. An example of such a sport elastic is the Dritz® Sport Elastic by Prym Consumer USA Inc., of Spartanburg, S.C., though other suitable materials can be used. Each outer band (23) of lower strap (22) is made from a second flexible material that is slightly elastic. In the illustrated embodiment, the second flexible material is different than the first flexible material and less elastic relative to the first flexible material. This may provide for sturdier straps for attaching lower strap (22). For instance, the second flexible material can be made from a stretchable fabric material. An example of such a sport elastic is the Bard® Deluxe Fabric Leg Straps by C.R. Bard Inc., of Murray Hill, N.J., though other suitable materials can be used. Further, a central portion of central band (26) is more elastic than each end portion of central band (26) where outer bands (23) are secured to central band (26). Still other suitable configurations for lower strap (22) will be apparent to one with ordinary skill in the art in view of the teachings herein. Accordingly, bands (26, 23) of lower strap (22) are sufficiently elastic and/or flexible to adjust about a user's leg.

Still referring to FIGS. 2-4B, upper strap (24) is similar to lower strap (22) in that upper strap (24) includes a central band (28) and a pair of outer bands (27) extending outwardly from each end portion of central band (28). Central band (28) has an interior surface (40) and an exterior surface (42). In the illustrated embodiment, each end portion of central band (28) is covered with a cap portion (41) that extends from the interior surface (40) around to the exterior surface (42). Cap portions (41) may include a sufficiently smooth material to provide comfort at each end portion of central band (28) to inhibit central band (28) from irritating a user's leg. It should be noted that cap portions (41) are merely optional.

Each outer band (27) has an interior surface (44) and an exterior surface (46). As best seen in FIG. 3A, interior surface (44) of each outer band (27) is secured to exterior surface (42) of central band (28). For instance, a first end (45) of each outer band (27) is secured to each end portion of central band (28) from first end (45) of outer band (27) to cap portion (41) of central band (28). Each outer band (27) may be coupled with central band (28) via sewing, adhesive, or other suitable methods. The portion of each outer band (27) secured to central band (28) includes a first coupling (43) on exterior surface (46) of outer band (27). Each outer band (27) then extends outwardly from central band (28) to a free end (49) of outer band (27). A portion of each outer band (27) at free end (49) includes a second coupling (47) on exterior surface (46) of outer band (27). A portion of second coupling (47) is configured to be selectively coupled with a portion of first coupling (43), as shown in FIGS. 3B and 4B. In the illustrated embodiment, first and second couplings (43, 47) comprise hook and loop fasteners, though other suitable couplings may be used, such as snaps, buttons, adhesives, etc. First and second couplings (43, 47) are positioned on exterior surface (46) of each outer band (27), which are coupled to exterior surface (42) of central band (28), such that interior surfaces (40, 44) of upper strap (24) are sufficiently smooth relative to exterior surfaces (42, 46). This may allow interior surfaces (40, 44) to be positioned against a user's leg to inhibit irritation and/or injuries to the user's leg.

Free end (49) of each outer band (27) further includes a handle (29) extending outwardly from free end (49) of each outer band (27). In the illustrated embodiment, each handle (29) is formed by a loop of material, though other suitable configurations for providing a suitable gripping portion may be used. Accordingly, handle (29) may be provided to allow a user to grip handle (29) to adjust the tightness of upper strap (24) about the user's leg even if the user has limited dexterity. In the illustrated embodiment, each handle (29) is sized to receive a user's thumb or finger within the loop of handle (29) for adjustment of upper strap (24). Handle (29) may be secured with each free end (49) of outer band (27) by sewing, adhesive, or other suitable method.

In the illustrated example, central band (28) of upper strap (24) has a greater width than the pair of outer bands (27). For instance, central band (28) may have a width of from about 1 inch to about 3 inches, such as about 2 inches, and each outer band (27) may have a width of from about ½ inch to about 1½ inches, such as about ¾ inches, though other suitable dimensions can be used. In some versions, the width of each outer band (27) is about 38% of the width of central band (28), though other suitable dimensions can be used. Central band (28) may have a length of about 13 inches to about 19 inches, though other suitable dimensions can be used. Each outer band (27) may have a length of from about 6 inches to about 12 inches, such as about 9½ inches, allowing each outer band (27) extends about 5 inches beyond central band (28), though other suitable dimensions can be used. Each handle (29) may have a length of from about 1 inch to about 2 inches and a width that is similar to the width of the corresponding outer band (27), though other suitable dimensions can be used. First coupling (43) may have a length of from about 1 inch to about 6 inches, such as about 4 inches and a width that is similar to the width of the corresponding outer band (27), though other suitable dimensions can be used. Second coupling (47) may have a length of from about ½ inch to about 2 inches, such as about 1 inch and a width that is similar to the width of the corresponding outer band (27), though other suitable dimensions can be used. Accordingly, second coupling (47) has a smaller length than first coupling (43). In some versions, second coupling may have a length that is about 25% of the length of first coupling (43), though other suitable dimensions can be used.

Figure 2:
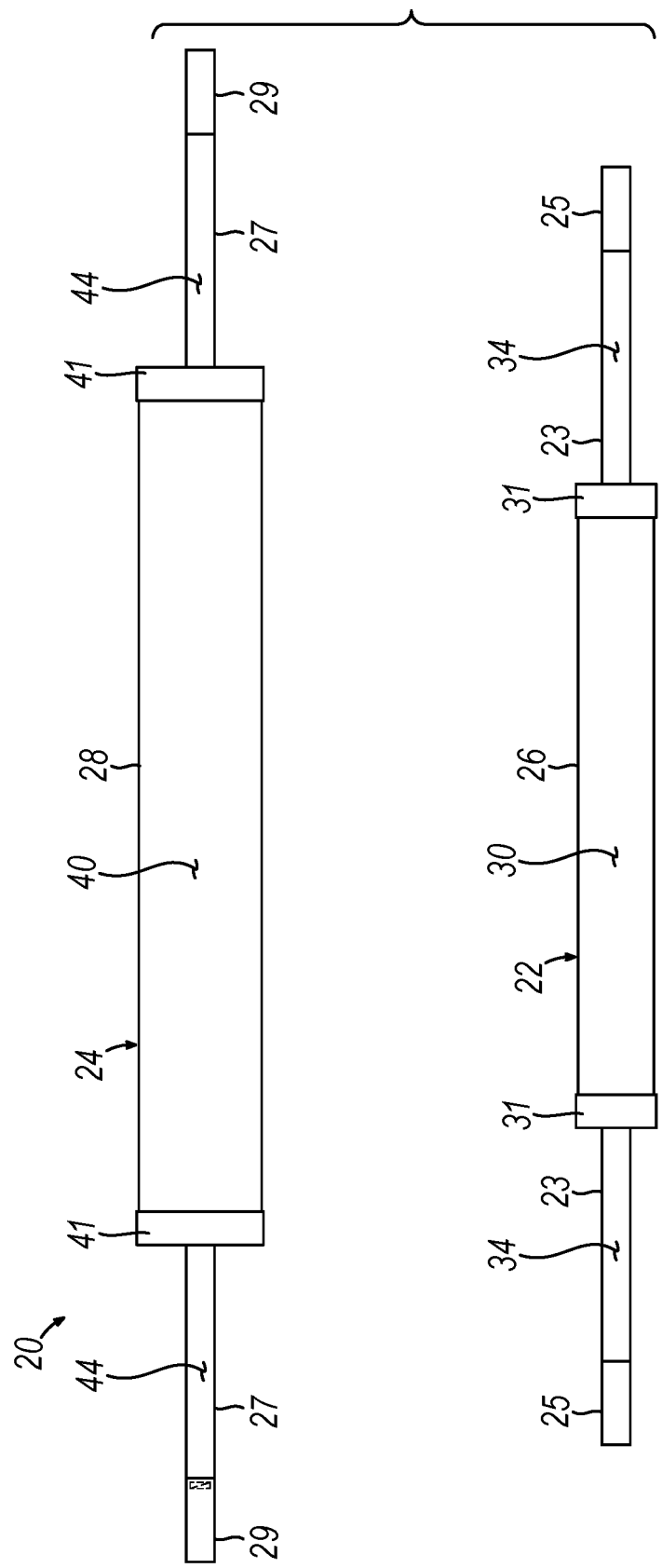
FIG. 2 depicts a front view of an exemplary leg strap assembly for use with a urine bag.

As best seen in FIG. 2, upper strap (24) has a larger width and/or length than lower strap (22) such that upper strap (24) may be positioned on an upper and/or thicker portion of a user's leg relative to lower strap (22). For instance, central band (28) of upper strap (24) may have a length that is from about a ½ inch to about 8½ inches longer than the length of central band (26) of lower strap (22), though other suitable dimensions can be used. Central band (28) of upper strap (24) may have a width that is about ¾ inches wider than the width of central band (26) of lower strap (22), though other suitable dimensions can be used. Each outer band (27) of upper strap (24) may have a length that extends outward from central band (28) that is about 1 inch longer than the length of each outer band (23) of lower strap (22) extending outward from central band (26), though other suitable dimensions can be used. Outer bands (27) of upper strap (24) may have a similar width to outer bands (23) of lower strap (22) such that outer bands (23, 27) are sufficient sized to be received through openings (18) of a urine bag (10). In some versions, lower and upper straps (22, 24) can be provide in various sizes (e.g., small, medium, large, etc.) such that leg strap assembly (20) can accommodate various sizes of different users.

Outer bands (27) of upper strap (24) may be made from the same second flexible material as outer bands (27) of lower strap (22). Central band (28) of upper strap (24) may be made from a third flexible material that is different than the first flexible material of central band (26) of lower strap (22) and the second flexible material of outer bands (23, 27). The third flexible material is sufficiently elastic to adjust to each user's leg, while being curl resistant. In the illustrated embodiment, the third flexible material is less elastic relative to the first flexible material more elastic relative to the second flexible material. For instance, central band (28) can be made from a knit elastic, which may comprise about 67% polyester and about 33% rubber. An example of such a knit elastic is the Dritz® Knit Elastic by Prym Consumer USA Inc., of Spartanburg, S.C., though other suitable materials can be used. Further, a central portion of central band (28) is more elastic than each end portion of central band (28) where outer bands (27) are secured to central band (28). Still other suitable configurations for upper strap (24) will be apparent to one with ordinary skill in the art in view of the teachings herein.

II. AN EXEMPLARY METHOD OF ATTACHING A LEG STRAP ASSEMBLY WITH A URINE BAG

Figure 5A:
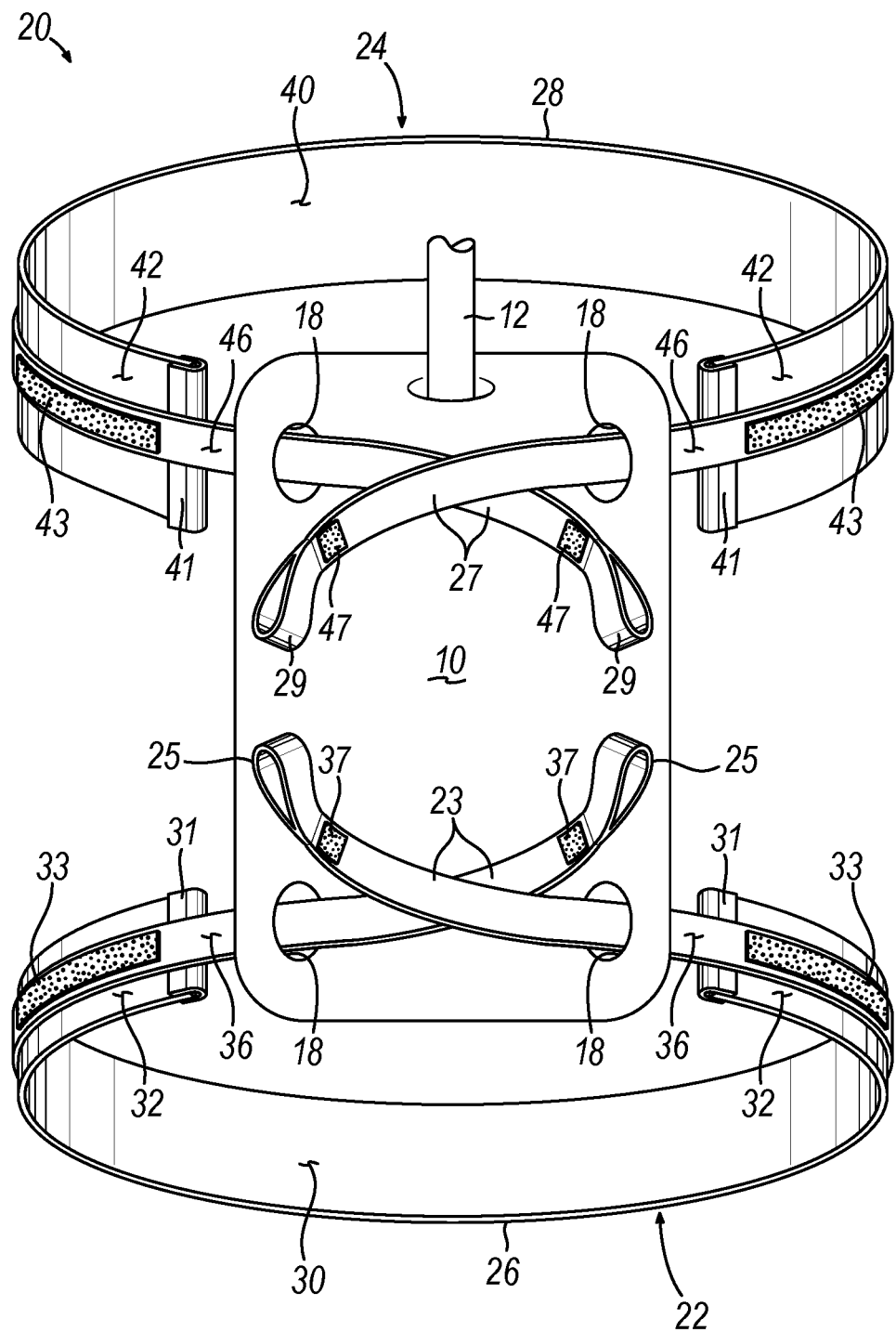
FIG. 5A depicts a perspective view of the leg strap assembly of FIG. 2 being inserted through openings of a urine bag in the unattached position.
Figure 5B:
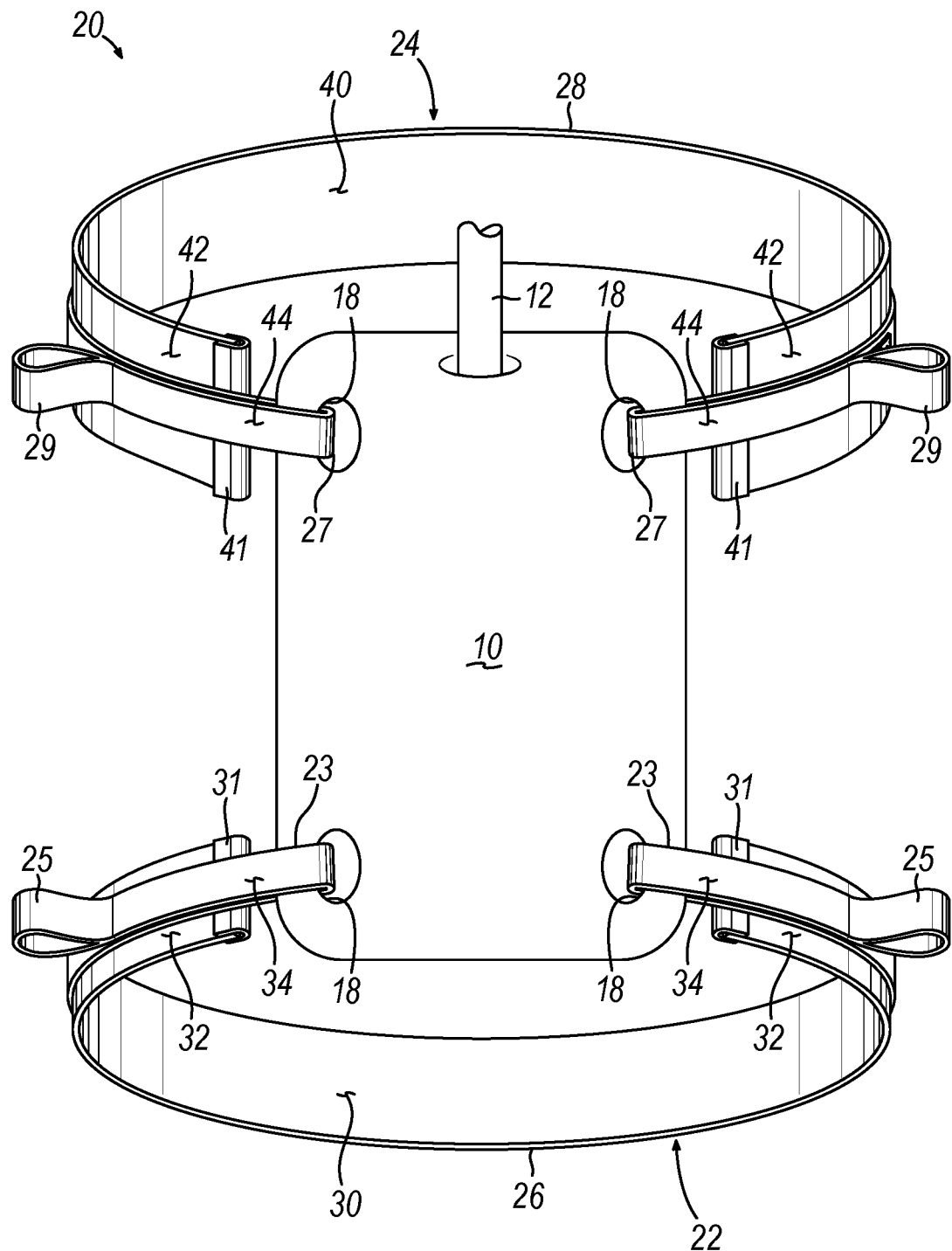
FIG. 5B depicts a perspective view of the leg strap assembly of FIG. 2 coupled with the urine bag in the attached position.
Figure 6:
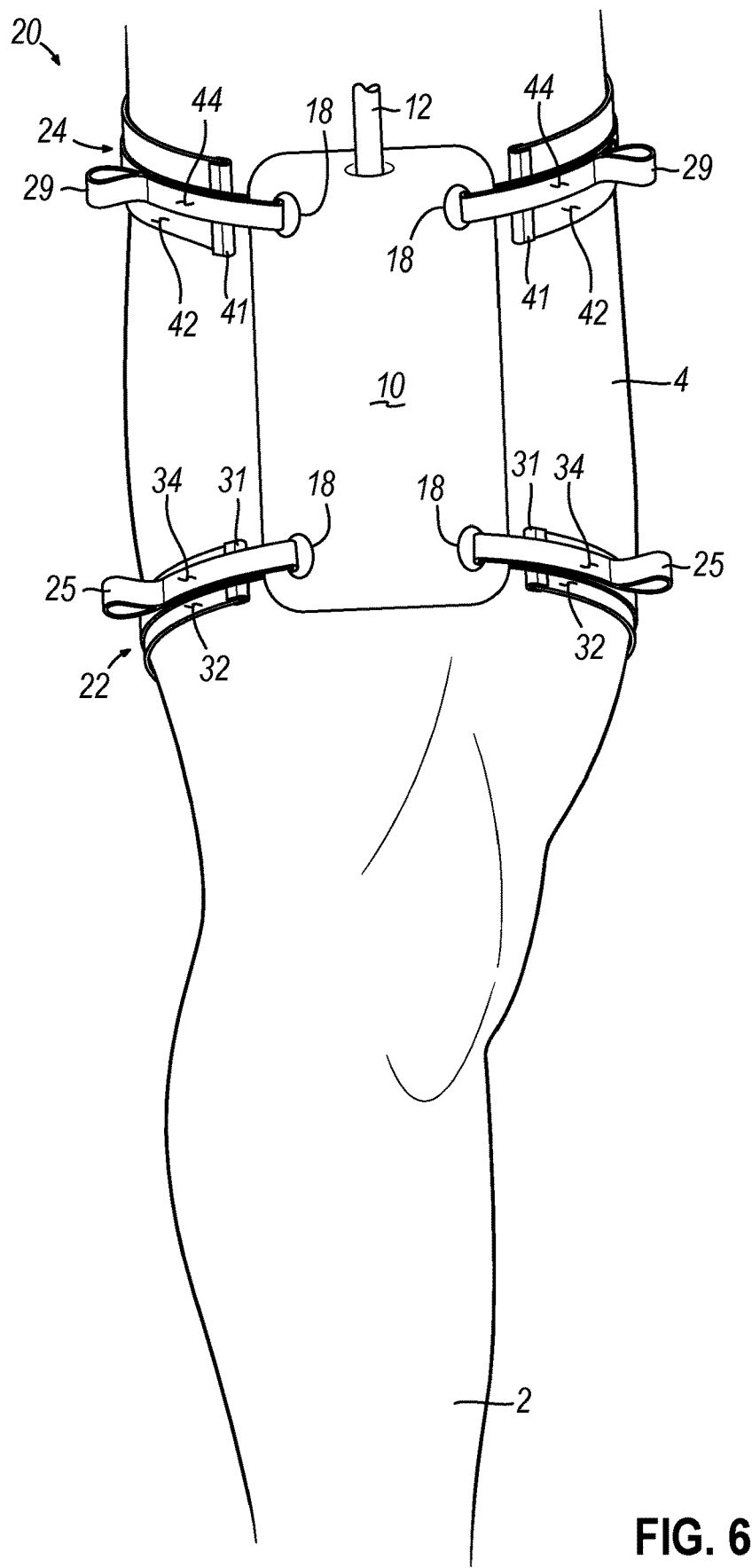
FIG. 6 depicts a schematic of the leg strap assembly of FIG. 2 shown attaching the urine bag to a leg of a user.

Referring to FIGS. 5A-6, leg strap assembly (20) can be used to couple a urine bag (10) to a user's leg, such as upper leg portion (4) (FIG. 6). For instance, interior surface (30) of central band (26) of lower strap (22) is positioned against the upper leg portion (4), such as above the user's knee. Accordingly, exterior surface (32) of central band (26), with couplings (33, 37), is positioned outward relative to the user's leg. Interior surface (40) of central band (28) of upper strap (24) is positioned against the upper portion (4) of the user's leg, above lower strap (22). Accordingly, exterior surface (42) of central band (28), with couplings (43, 47), is positioned outward relative to the user's leg. Handles (25, 29) and/or free ends (39, 49) of each lower and upper strap (22, 24) can then be grasped and inserted through corresponding openings (18) of the urine bag (10). Outer bands (23, 27) of each lower and upper strap (22, 24) can then be pulled through openings (18) of urine bag (10) to adjust the tightness of straps (22, 24) around the leg. Once a desired tightness is achieved, each outer band (23, 27) of lower and upper straps (22, 24) are bent outward toward the corresponding central band (26, 28).

A portion of each second coupling (37, 47) can then be coupled with a portion of the corresponding first coupling (33, 43) to selectively couple outer bands (23, 27) with central bands (26, 28). In the illustrated embodiment, a portion of second couplings (37, 47) are aligned with and pressed against a portion of first couplings (33, 43) to thereby engage the hook and loop fasteners of first and second couplings (33, 43, 37, 47) to maintain the position of second couplings (37, 47) relative to first couplings (33, 43). Couplings (33, 43, 37, 47) thereby maintain the position of outer bands (23, 27) relative to central bands (26, 28) of lower and upper straps (22, 24) to allow leg strap assembly (20) to support urine bag (10) relative to the upper portion (4) of a user's leg.

Once leg strap assembly (20) is secured, the tightness of leg strap assembly (20) may be adjusted. For instance, a user may grasp handles (25, 29) and/or free ends (39, 49) of lower and/or upper straps (22, 24) to release second couplings (37, 47) from first couplings (33, 43). Outer bands (23, 27) can then be tightened and/or loosened relative to the user's leg. Second couplings (37, 47) may then be recoupled with first couplings (33, 43). Additionally, or alternatively, leg strap assembly (20) can be released to remove urine bag (10) from leg strap assembly (20). Once second couplings (37, 47) are released from first couplings (33, 43), outer bands (23, 27) may be removed through openings (18) of urine bag (10) to remove urine bag (10) from leg strap assembly (20).

In some versions, leg strap assembly (20) can be worn under capable clothing pants to allow for easier access to urine bag (10). An example of capable clothing pants is provided in U.S. Patent Pub. No. 2018/0289085, entitled "Capable Clothing Pants," published on Oct. 11, 2018, the disclosure of which is incorporated by reference herein.

Accordingly, leg strap assembly (20) provides lower and upper straps (22, 24) that allow straps (22, 24) to be attached to an upper leg portion (4) of the user to reduce injury during emptying and/or changing urine bag (10). The wider width of central bands (26, 28) of lower and upper straps (22, 24) relative to outer bands (23, 27) further provide more comfort to reduce injury during wearing urine bag (10). Still other suitable configurations and/or methods of using leg strap assembly (20) will be apparent to one with ordinary skill in the art in view of the teachings herein.

III. EXAMPLES

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A leg strap assembly for supporting a urine bag, wherein the leg strap assembly comprises: a lower strap having a central band and a pair of outer bands extending outward from each end portion of the central band; and an upper strap having a central band and a pair of outer bands extending outward from each end portion of the central band; wherein the outer bands of each of the lower and upper straps are selectively couplable with the urine bag, wherein the lower and upper straps are sufficiently sized to wrap around at least a portion of an upper leg portion to support the urine bag on the upper leg portion.

Example 2

The leg strap assembly of example 1, wherein the upper strap is positioned above the lower strap on the upper leg portion.

Example 3

The leg strap assembly of any of examples 1 through 2, wherein the central band of the upper strap has a larger width than each of the outer bands of the upper strap, and wherein the central band of the lower strap has a larger width than each of the outer bands of the lower strap.

Example 4

The leg strap assembly of any of examples 1 through 3, wherein the central band of the upper strap has a larger width than the central band of the lower strap.

Example 5

The leg strap assembly of any of examples 1 through 4, wherein the central band of the upper strap has a larger length than each of the outer bands of the upper strap, and wherein the central band of the lower strap has a larger length than each of the outer bands of the lower strap.

Example 6

The leg strap assembly of any of examples 1 through 5, wherein the central band of the upper strap has a larger length than the central band of the lower strap.

Example 7

The leg strap assembly of any of examples 1 through 6, wherein each outer strap of the upper strap has a larger length than each outer band of the lower strap.

Example 8

The leg strap assembly of any of examples 1 through 7, wherein the central band of the lower strap is made from a first flexible material, wherein each outer band of the lower strap is made from a second flexible material that is different than the first flexible material, wherein the first flexible material is more elastic relative to the second flexible material.

Example 9

The leg strap assembly of example 8, wherein the central band of the upper strap is made from a third flexible material that is different than the first and second flexible material, wherein the first flexible material is more elastic relative to the third flexible material, wherein the third flexible material is more elastic relative to the second flexible material.

Example 10

The leg strap assembly of any of examples 1 through 9, wherein the central band of the lower strap is made from a flexible material, wherein the central band of the upper strap is made from another flexible material that is different than the flexible material of the lower strap, wherein the flexible material of the lower strap is more elastic relative to the flexible material of the upper strap.

Example 11

The leg strap assembly of any of examples 1 through 10, wherein an exterior surface of each outer band of the lower strap is attached to an interior surface of the central band of the lower strap, and wherein an exterior surface of each outer band of the upper strap is attached to an interior surface of the central band of the upper strap.

Example 12

The leg strap assembly of any of examples 1 through 11, wherein each outer band of the lower strap includes a first coupling and a second coupling that is selectively couplable with the first coupling to maintain the position of the lower strap relative to the upper leg portion, and wherein each outer band of the upper strap includes a first coupling and a second coupling that is selectively couplable with the first coupling to maintain the position of the upper strap relative to the upper leg portion.

Example 13

The leg strap assembly of example 12, wherein the first coupling of each outer band of the lower strap is positioned on an exterior surface of the outer band at an end portion of the outer band coupled to the central band, wherein the second coupling of each outer band of the lower strap is positioned on an exterior surface of the outer band at a free end portion of the outer band outward of the central band, wherein the first coupling of each outer band of the upper strap is positioned on an exterior surface of the outer band at an end portion of the outer band coupled to the central band, wherein the second coupling of each outer band of the upper strap is positioned on an exterior surface of the outer band at a free end portion of the outer band outward of the central band.

Example 14

The leg strap assembly of any of examples 1 through 13, wherein each end portion of the central band of the lower strap includes a cap portion extending from an interior surface to an exterior surface of each end portion of the central band, and wherein each end portion of the central band of the upper strap includes a cap portion extending from an interior surface to an exterior surface of each end portion of the central band.

Example 15

The leg strap assembly of any of examples 1 through 14, wherein a free end of each outer band of the lower strap includes a handle extending outward from each free end, wherein the handle is configured to be grasped by a user to adjust the position of the lower strap relative to the upper leg portion, and wherein a free end of each outer band of the upper strap includes a handle extending outward from each free end, wherein the handle is configured to be grasped by a user to adjust the position of the upper strap relative to the upper leg portion.

Example 16

The leg strap assembly of any of examples 1 through 15, wherein each outer band of the lower and upper straps are sufficiently sized to be received by corresponding openings of a urine bag to selectively couple the leg strap assembly with the urine bag.

Example 17

A leg strap assembly for supporting a urine bag, wherein the leg strap assembly comprises a pair of straps selectively couplable with the urine bag, wherein each strap of the leg strap assembly includes a central band and a pair of outer bands extending outward from each end portion of the central band, wherein the central band has a larger width than the each of the outer bands.

Example 18

The leg strap assembly of example 17, wherein the pair of straps are sufficiently sized to wrap around at least a portion of an upper leg portion to support the urine bag on the upper leg portion.

Example 19

The leg strap assembly of any of examples 17 through 18, wherein the central band is made from a first flexible material, wherein each outer band is made from a second flexible material that is different than the first flexible material, wherein the first flexible material is more elastic relative to the second flexible material.

Example 20

A method of coupling a leg strap assembly to a urine bag, wherein the leg strap assembly comprises a lower strap having a central band and a pair of outer bands extending outward from each end portion of the central band, and an upper strap having a central band and a pair of outer bands extending outward from each end portion of the central band, wherein the method comprises the steps of: positioning an interior surface of the central band of the lower strap against an upper leg portion; positioning an interior surface of the central band of the upper strap against an upper leg portion above the lower strap; inserting a free end of each outer band of the lower and upper straps through a corresponding opening of the urine bag; bending each outer band outward toward an exterior surface of the corresponding central band; and coupling a first coupling on an exterior surface of each outer band of the lower and upper straps to a second coupling on the exterior surface of each outer band to maintain the position of the lower and upper straps relative to the upper leg portion.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A leg strap assembly for supporting a urine bag, wherein the leg strap assembly comprises:
   (a) a lower strap having:
      i. a first central band extending between a first end and a second end; and
      ii. a first pair of outer bands, comprising:
         1. A first outer band, and
         2. a second outer band,
         wherein:
            A. the first outer band extends outward from the first end of the first central band, and
            B. the second outer band extends outward from the second end of the first central band; and
   (b) an upper strap having:
      i. a second central band extending between a third end and a fourth end; and
      ii. a second pair of outer bands, comprising:
         1. A third outer band, and
         2. a fourth outer band,
         wherein:
            A. the third outer band extends outward from the third end of the second central band, and
            B. the fourth outer band extends outward from the fourth end of the second central band;
   and further wherein:
      (A) the first, second, third and fourth outer bands are each selectively couplable with the urine bag,
      (B) the lower and upper straps are sufficiently sized to wrap around at least a portion of an upper leg portion to support the urine bag on the upper leg portion, and
      (C) the first and second outer bands are each selectively couplable with the urine bag by forming a respective loop such that the first and second outer bands selectively couple back onto themselves,
   and further wherein:
      (a) each of the first and second outer bands has a free end disposed distally from an attached end, wherein the attached end is proximate to the first central band of the lower strap, wherein:
         i. each of the free ends of the first and second outer bands includes first and second handles respectively extending outward from each of the free ends of the first and second outer bands, wherein the first and second handles have first and second loops of material, and
         ii. each of the first and second loops is configured to be grasped by a user to adjust a position of the lower strap relative to the upper leg portion; and
      (b) each of the third and fourth outer bands has a free end disposed distally from the second central band of the upper strap, wherein:
         i. the free ends of the third and fourth outer bands of the upper strap include third and fourth handles, respectively, extending outward from the free ends, wherein the third and fourth handles have third and fourth loops of material, and
         ii. each of the third and fourth loops of the third and fourth outer bands is configured to be grasped by a user to adjust a position of the upper strap relative to the upper leg portion,
   wherein each of the first, second, third, and fourth bands extends continuously from the respective attached end to the respective free end with a uniform width, wherein each of the first, second, third, and fourth loops also has a uniform width.

2. The leg strap assembly of claim 1, wherein the second central band of the upper strap has a larger width than the first central band of the lower strap.

3. The leg strap assembly of claim 1, wherein the second central band of the upper strap has a longer length than each of the third and fourth outer bands of the upper strap, and wherein the first central band of the lower strap has a longer length than each of the first and second outer bands of the lower strap.

4. The leg strap assembly of claim 1, wherein the second central band of the upper strap has a longer length than the first central band of the lower strap.

5. The leg strap assembly of claim 1, wherein each of the third and fourth outer bands has a longer length than each of the first and second outer bands.

6. The leg strap assembly of claim 1, wherein the first central band of the lower strap is made from a first flexible material, wherein each of the first and second outer bands is made from a second flexible material that is different than the first flexible material, wherein the first flexible material is more elastic relative to the second flexible material.

7. The leg strap assembly of claim 6, wherein the second central band of the upper strap is made from a third flexible material that is different than the first and second flexible material, wherein the first flexible material is more elastic relative to the third flexible material, wherein the third flexible material is more elastic relative to the second flexible material.

8. The leg strap assembly of claim 1, wherein the first central band of the lower strap is made from a flexible material, wherein the second central band of the upper strap is made from another flexible material that is different than the flexible material of the lower strap, wherein the flexible material of the lower strap is more elastic relative to the flexible material of the upper strap.

9. The leg strap assembly of claim 1, wherein an exterior surface of each of the first and second outer bands is attached to an interior surface of the first central band of the lower strap, and wherein an exterior surface of each of the third and fourth outer bands is attached to an interior surface of the second central band of the upper strap.

10. The leg strap assembly of claim 1, wherein:
    (a) to maintain the position of the lower strap relative to the lower leg portion:
       i. the first outer band includes a first coupling and a second coupling, wherein the second coupling is selectively couplable with the first coupling,
       ii. the second outer band includes a third coupling and a fourth coupling, wherein the fourth coupling is selectively couplable with the third coupling,
    (b) to maintain the position of the lower strap relative to the lower leg portion:
       i. the third outer band includes a fifth coupling and a sixth coupling, wherein the sixth coupling is selectively couplable with the fifth coupling, and
       ii. the fourth outer band includes a seventh coupling and an eighth coupling, wherein the seventh coupling is selectively couplable with the eighth coupling.

11. The leg strap assembly of claim 10, wherein:
    (a) the first coupling of the first outer band of the lower strap is positioned on an exterior surface of the first outer band at a first end portion of the first outer band coupled to the first central band, (b) the second coupling of the first outer band of the lower strap is positioned on an exterior surface of the first outer band at a second end portion of the first outer band at an end portion of the first outer band coupled to the first central band, (c) the fifth coupling of the third outer band of the upper strap is positioned on an exterior surface of the third outer band at an end portion of the third outer band coupled to the second central band, wherein the fifth coupling of the third outer band of the upper strap is positioned on an exterior surface of the third outer band at a free end portion of the third outer band outward of the second central band.

12. The leg strap assembly of claim 1, wherein;

(a) each of the first and second ends of the first central band of the lower strap includes a cap portion extending from an interior surface to an exterior surface of each of the first and second ends of the first central band, and (b) each of the third and fourth ends of the second central band of the upper strap includes a cap portion extending from an interior surface to an exterior surface of each of the third and fourth ends of the second central band.

13. The leg strap assembly of claim 1, wherein each of the first, second, third and fourth outer bands of the lower and upper straps are sufficiently sized to be received by corresponding openings of a urine bag to selectively couple the leg strap assembly with the urine bag.

14. The leg strap assembly of claim 1, wherein the first, second, third, or fourth loops of material are configured to receive a user's thumb or finger within each loop, wherein each loop is sized to be passed through a corresponding opening of a urine bag, wherein the loops are configured to allow a user to adjust the tightness of the upper and lower straps about the user's leg even if the user has limited dexterity to selectively couple the urine bag to the user's leg.

15. The leg strap of claim 14, wherein each loop of material has a width that is equal to a width of a remaining portion of each of the first, second, third, and fourth bands.

16. The leg strap of claim 10, wherein the first, third, fifth, and seventh couplings are spaced apart from each free end of the respective outer band in a direction towards the central band away from each respective handle.

17. A method of coupling a leg strap assembly of claim 1 to a urine bag, wherein the method comprises the steps of:

(a) positioning an interior surface of the first central band of the lower strap against an upper leg portion;

(b) positioning an interior surface of the second central band of the upper strap against an upper leg portion above the lower strap;

(c) inserting the loop positioned on the free end of each pair of outer bands of the lower and upper straps through a corresponding unobstructed opening of the urine bag;

(d) pulling each loop with a finger or thumb outward toward an exterior surface of the corresponding central band until a desired tightness is obtained; and (e) coupling a first coupling on an exterior surface of each of the pair of outer bands of the lower and upper straps to a second coupling on the exterior surface of each of the pair of outer bands to maintain the position and tightness of the lower and upper straps relative to the upper leg portion.

18. The method of claim 17, wherein the first coupling is spaced apart from the free end in a direction towards the central band.

* * * * *